United States Patent [19]

Gubelmann et al.

[11] Patent Number: 4,982,013

[45] Date of Patent: Jan. 1, 1991

[54] PREPARATION OF POLYHYDROXYBENZENES BY DIRECT HYDROXYLATION OF PHENOLS

[75] Inventors: Michel Gubelmann, Lyon; Philippe-Jean Tirel, Oullins, both of France

[73] Assignee: Rhone-Poulenc Chimie, Courbevoie, France

[21] Appl. No.: 346,215

[22] Filed: May 2, 1989

[30] Foreign Application Priority Data

May 2, 1988 [FR] France ................................ 88 05849

[51] Int. Cl.$^5$ ........................ C07C 37/60; C07C 39/08
[52] U.S. Cl. ..................................... 568/771; 568/767
[58] Field of Search ............... 568/767, 771, 763, 800

[56] References Cited

U.S. PATENT DOCUMENTS 1,547,725  7/1925  Bibb ................................ 568/800 X
4,578,521  3/1986  Chang et al. ......................... 568/771

OTHER PUBLICATIONS

Suzuki et al, "Chemical Abstracts", vol. 109(10), p. 75661u (1988).
Iwamoto, "Patent Abstracts of Japan", vol. 10, No. 31(C-327) (1986), JP-A-60 184 036.
Iwamoto et al, "The Journal of Physical Chemistry", vol. 87, No. 6, 17 Mar. 1983, pp. 903-905.

*Primary Examiner*—Werren B. Lone
*Attorney, Agent, or Firm*—Burns, Doane, Swecker & Mathis

[57] ABSTRACT

Polyhydroxybenzenes, e.g., the dihydroxybenzenes, are prepared by directly hydroxylating a phenol with nitrous oxide, preferably in vapor phase, on a substrate of acidified zeolite particulates, advantageously ZSM-5 zeolite particulates, and such acidified zeolite particulates advantageously having a molar ratio $SiO_2/Al_2O_3$ of greater than about 90, preferably up to 500.

11 Claims, No Drawings

PREPARATION OF POLYHYDROXYBENZENES BY DIRECT HYDROXYLATION OF PHENOLS

CROSS-REFERENCE TO COMPANION APPLICATION

Our copending application, Ser. No. 346,216 [Attorney Docket No. 022700-896], filed concurrently herewith and assigned to the assignee hereof.

BACKGROUND OF THE INVENTION

1. Field of the Invention:

The present invention relates to the preparation of dihydroxybenzenes and, more especially, to the preparation of dihydroxybenzenes by the hydroxylation of phenols.

2. Description of the Prior Art:

The hydroxylation of phenol or of substituted phenols using hydrogen peroxide to prepare diphenols has long been known to this art.

French Patent FR No. 2,071,464 describes a process in which such reaction is catalyzed by a strong acid, such as, for example, perchloric acid or sulfuric acid.

German Patent No. 2,410,742 describes a process similar to that of the '464 patent, in which the hydrogen peroxide is employed in the form of a virtually anhydrous organic solution.

The above two processes have attracted considerable interest and the former is used industrially.

However, for a considerable period of time, this art has sought to catalyze the hydroxylation reaction by means of solids which are undissolved in the reaction medium, in order to simplify their separation therefrom, to permit the optional recycling thereof, and to avoid saline byproducts which are principally formed during removal of the dissolved acid catalysts.

Thus, French Patent FR No. 2,489,816 recommends the use of titanium silicalite as a heterogeneous catalyst for the hydroxylation of aromatic compounds by means of hydrogen peroxide.

However, such catalysis presents extreme problems of reproducibility. Moreover, the fine size of these catalyst particles makes their separation from the reaction medium very difficult and their recycling problematical, while in an industrial process, it is essential to be able to recycle an expensive catalyst.

In order to remedy this problem of separation of the catalyst, it has been proposed, in the European Patent Application published under No. 200,260, to employ agglomerates of these fine particles of titanium silicalite.

The difficulty in controlling the reliability of plant installations when using hydrogen peroxide for hydroxylation and the mediocrity of the prior art yields have long prompted those skilled in this art to seek, essentially unsuccessfully, to introduce a hydroxyl group directly onto the phenolic ring in the absence of any peroxide derivative.

The only publication describing the direct introduction of a hydroxyl group onto a benzene nucleus is believed to be the article by Iwamoto, published in the *Journal of Physical Chemistry*, 87, 6 (1983).

Such benzene hydroxylation reaction is carried out by means of nitrous oxide ($N_2O$) in the presence of a catalyst based on an oxide of a metal of Groups V or VI of the Periodic Table.

Vanadium oxide is the preferred oxide among the oxides of the metals of Groups V and VI of the Periodic Table. It is more preferred to employ such oxide distributed on a substrate based on silica, in an amount by weight ranging from 1% to 10% relative to the substrate. The substrate preferably is constituted of silica, since alumina in most cases causes the formation of a mixture of the oxides of carbon.

This particular process was of interest, but the requirement for special catalysts made it relatively unattractive to industry.

Thus, serious need continues to exist in this art for a process for the direct hydroxylation of the benzene nucleus on a simple and readily available substrate.

SUMMARY OF THE INVENTION

Accordingly, a major object of the present invention is the provision of an improved process for the preparation of polyhydroxybenzenes by the direct hydroxylation of phenols.

Briefly, the present invention features the preparation of dihydroxybenzenes by contacting phenols with nitrous oxide on an acidified zeolite.

DETAILED DESCRIPTION OF THE PREFERRED EMBODIMENTS OF THE INVENTION

More particularly according to the present invention, exemplary of the zeolite substrates are the commercial forms thereof, such as:

(i) zeolite ZSM-5 (marketed by Mobil), the preparation of which is described in the U.S. Pat. No. 3,702,886;

(ii) zeolite US-Y (marketed by Toyo-Soda);

(iii) zeolite HY (marketed by Union Carbide), under the grade number LZY 82; and (iv) zeolite H-Mordenite (marketed by La Grande Paroisse).

Preferably, the commercial zeolite ZSM-5 is used.

The zeolite preferably has a ratio $SiO_2/Al_2O_3$ greater than 90 and even more preferably ranging from 90 to 500.

According to the present invention, the commercial zeolite is preferably acidified by addition thereto of an inorganic acid selected from among hydrochloric acid, sulfuric acid, nitric acid, perchloric acid and phosphoric acid, or by the addition of an organic acid selected from among halosulfonic acids, halomethanesulfonic acids and halocarboxylic acids, and preferably trifluoromethanesulfonic acid.

In a preferred embodiment of the invention, the zeolite is acidified by soaking it in a volume of acid having a normality of from 0.1N to 2N, in an amount of from 10 ml/g to 100 ml/g, per gram of zeolite. Such soaking may be carried out in a single step or, preferably, in several successive steps.

Nitrous oxide is employed pure, or in admixture with an inert gas which does not contain any oxygen, such as nitrogen.

The phenol is preferably introduced in admixture with nitrous oxide, in a molar ratio of nitrous oxide to the phenol ranging from 1 to 10.

In another preferred embodiment of the invention, the phenol is vaporized, is next mixed with the nitrous oxide in the proportions given above, and is then circulated over the zeolite. The reaction is preferably carried out at a temperature of from 300° and 500° C.

The gases evolved from the reaction comprise a mixture of dihydroxybenzenes, hydroquinone, pyrochatecol, and resorcinol and are condensed and separated by any technique known to this art.

In order to further illustrate the present invention and the advantages thereof, the following specific examples are given, it being understood that same are intended only as illustrative and in nowise limitative.

In said examples to follow, the following abbreviations were used:

$TT$ = degree of conversion = $\dfrac{\text{product converted}}{\text{product introduced}}$ in mols $RT$ = yield based on product converted = $\dfrac{\text{product desired}}{\text{product converted}}$ in mols

EXAMPLES 1 and 2

Preparation of the catalyst 10 g of commercial zeolite NaZSM-5 were contacted with 100 ml of 1N HCl solution at 60° C. for 4 hours under stirring. The mixture was permitted to cool and was washed with deionized water. The solids were filtered and dried in an oven at 100° C.

The washing procedure described above was repeated 4 times. The dried product obtained after the fourth washing was ground.

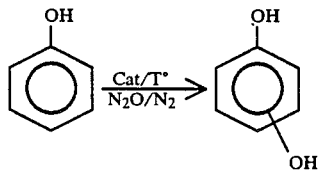

EXPERIMENTAL CONDITIONS

| Vapor phase | continuous |
|---|---|
| Catalyst | HZSM-5 |
| | diameter of pores: 550 pm |
| | Ratio $\dfrac{SiO_2}{Al_2O_3}$ = 120 |
| Temperature | 400° C. and 450° C. |
| Contact time | about 1 second |
| Molar ratio | phenol/$N_2$/$N_2O$ 2/5/8 |

1.05 g of catalyst HZSM-5 ($SiO_2/Al_2O_3$=120) in powder form, dispersed in 4 g of quartz grains (<0.8 mm), were introduced into a tubular reactor constructed of quartz (length=16 cm, internal diameter=1.8 cm).

Subsequently, a 10 cm bed of glass beads was added, whereupon the gaseous mixture became homogenized. The reactor which had been charged in this fashion was conditioned for 15 hours at 350° C. under nitrogen in a tubular The reaction was carried out continuously by introducing 1.4 cm$^3$/h of phenol, 1.44 l/h of nitrous oxide and 0.9 l/h of nitrogen.

The results are reported in the following Table:

TABLE

| EXAMPLE | T° | TT PHENOL % | RT (TOTAL) dihydroxybenzene | DISTRIBUTION OF ISOMERS | | |
|---|---|---|---|---|---|---|
| | | | | ORTHO | META | PARA |
| 1 | 400° C. | 5 | 87 | 30 | 33 | 37 |
| 2 | 450° C. | 4.5 | 82 | 30 | 40 | 30 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the present invention be limited solely by the scope of the following claims, including equivalents thereof.

What is claimed is:

1. A process for the preparation of a dihydroxybenzene, comprising directly hydroxylating a phenol with nitrous oxide on a substrate of acidified zeolite particulates.

2. The process as defined by claim 1, said acidified zeolite particulates having a molar ratio $SiO_2/Al_2O_3$ greater than about 90.

3. The process as defined by claim 2, said acidified zeolite particulates comprising a HZSM-5 zeolite, an HY zeolite or H-mordenite zeolite having a molar ratio $SiO_2/Al_2O_3$ ranging from 90 to 500.

4. The process as defined by claim 3, said acidified zeolite particulates comprising a ZSM-5 zeolite.

5. The process as defined by claim 1, said zeolite particulates having been acidified with an inorganic acid.

6. The process as defined by claim 5, said inorganic acid comprising hydrochloric acid, sulfuric acid, nitric acid, perchloric acid, or phosphoric acid.

7. The process as defined by claim 1, wherein the molar ratio of nitrous oxide to phenol ranges from 1 to 10.

8. The process as defined by claim 1, wherein said nitrous oxide is admixed with an inert gas.

9. The process as defined by claim 8, said inert gas comprising nitrogen.

10. The process as defined by claim 1, comprising vaporizing the phenol, admixing it with the nitrous oxide, and circulating the admixture over the acidified zeolite particulates.

11. The process as defined by claim 1, carried out at a temperature ranging from 300° to 500° C.

* * * * *